(12) United States Patent
Bay et al.

(10) Patent No.: US 10,899,799 B2
(45) Date of Patent: Jan. 26, 2021

(54) METHOD FOR PREPARING MULTIPLE ANTIGEN GLYCOPEPTIDE CARBOHYDRATE CONJUGATES

(71) Applicants: Institut Pasteur, Paris (FR); Centre National de la Recherche Scientifique, Paris (FR)

(72) Inventors: Sylvie Bay, Paris (FR); Claude Leclerc, Paris (FR); Richard Lo-Man, Paris (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 463 days.

(21) Appl. No.: 15/444,547

(22) Filed: Feb. 28, 2017

(65) Prior Publication Data
US 2017/0283466 A1 Oct. 5, 2017

Related U.S. Application Data

(63) Continuation of application No. 14/005,336, filed as application No. PCT/IB2012/051285 on Mar. 16, 2012, now abandoned.

(30) Foreign Application Priority Data

Mar. 17, 2011 (EP) ..................................... 11290138

(51) Int. Cl.
| | | |
|---|---|---|
| *C07K 9/00* | (2006.01) | |
| *C07K 14/74* | (2006.01) | |
| *A61K 47/64* | (2017.01) | |
| *A61K 47/55* | (2017.01) | |

(52) U.S. Cl.
CPC ............. *C07K 9/00* (2013.01); *A61K 47/55* (2017.08); *A61K 47/645* (2017.08); *C07K 9/001* (2013.01); *C07K 14/70539* (2013.01)

(58) Field of Classification Search
CPC .... C07K 9/00; C07K 9/001; C07K 14/70539; C07K 7/00; C07K 7/08; A61K 47/481; A61K 47/48315
See application file for complete search history.

(56) References Cited

U.S. PATENT DOCUMENTS

| | | | | |
|---|---|---|---|---|
| 5,837,243 A | * | 11/1998 | Deo .................. | C07K 14/33 424/136.1 |
| 6,676,946 B2 | | 1/2004 | Bay et al. | |
| 2003/0083235 A1 | * | 5/2003 | Danishefsky .......... | C07K 9/001 424/185.1 |

FOREIGN PATENT DOCUMENTS

| | | |
|---|---|---|
| WO | WO 93/21948 A1 | 11/1993 |
| WO | WO 98/43677 | 10/1998 |

OTHER PUBLICATIONS

Lo-Man et al., Anti-Tumor Immunity Provided by a Synthetic Multiple Antigenic Glycopeptide Displaying a Tri-Tn Glycotope, J. Immun. 2001, 166:2849-2854.*
Lo-Man et al., Anti-Tumor Immunity Provided by a Synthetic Multiple Antigenic Glycopeptide Displaying a Tri-Tn Glycotope, J. Immun. 2001, 166:2849-2854 (Year: 2001).*
Fmoc Solid Phase Peptide Synthesis, Chan and White, Eds., Oxford Univ. Press, 2000, pp. 11-13, 27, 29 (Year: 2000).*
Bay et al., "Preparation of a multiple antigen glycopeptide (MAG) carrying the Tn antigen", J. Peptide Res., 1997, 49:620-625. (Year: 1997).*
Lo-Man et al., "Anti-Tumor Immunity Provided by a Synthetic Multiple Antigenic Glycopeptide Displaying a Tri-Tn Glycopeptide", J. Immun. 2011, 166:2849-2854 (Year: 2011).*
International Search Report for Application No. PCT/IB2012/051285 dated May 29, 2012.
Bay et al., Preparation of a multiple antigen glycopeptide (MAG) carrying the Tn antigen. A possible approach to a synthetic carbohydrate vaccine. J Pept Res. Jun. 1997;49(6):620-5.
Bolscher et al., Solid-phase synthesis of a pentavalent GalNAc-containing glycopeptide (Tn antigen) representing the nephropathy-associated IgA hinge region. Carbohydr Res. Sep. 23, 2010;345(14):1998-2003. doi: 10.1016/j.carres.2010.07.022. Epub Jul. 17, 2010.
Buskas et al., Immunotherapy for cancer: synthetic carbohydrate-based vaccines. Chem Commun (Camb). Sep. 28, 2009;(36):5335-49. doi: 10.1039/b908664c. Epub Jul. 22, 2009.
Ingale et al., Robust immune responses elicited by a fully synthetic three-component vaccine. Nat Chem Biol. Oct. 2007;3(10):663-7. Epub Sep. 2, 2007.
Jayaraman et al., Synthetic carbohydrate-containing dendrimers. Chem Eur J. 1997;3(8):1190-1204.
Kaminskas et al., Pharmacokinetics and tumor disposition of PEGylated, methotrexate conjugated poly-l-lysine dendrimers. Mol Pharm. Jul.-Aug. 2009;6(4):1190-204. doi: 10.1021/mp900049a.
Kuduk et al., Synthetic and immunological studies on clustered modes of mucin-related Tn and TF O-linked antigens: The preparation of a glycopeptide-based vaccine for clinical trials against prostate cancer. J Am Chem Soc. 1998;120(48):12474-85.
Lo-Man et al., A fully synthetic therapeutic vaccine candidate targeting carcinoma-associated Tn carbohydrate antigen induces tumor-specific antibodies in nonhuman primates. Cancer Res. Jul. 15, 2004;64(14):4987-94.

(Continued)

*Primary Examiner* — Lianko G Garyu
(74) *Attorney, Agent, or Firm* — Birch, Stewart, Kolasch & Birch, LLP

(57) ABSTRACT

The present invention relates to a method for preparing carbohydrate T cell epitope conjugates of formula (I): $M(T-B)_n$ (I) wherein M, T, B and n ore as defined in claim 1.

13 Claims, 2 Drawing Sheets

Figure 1:
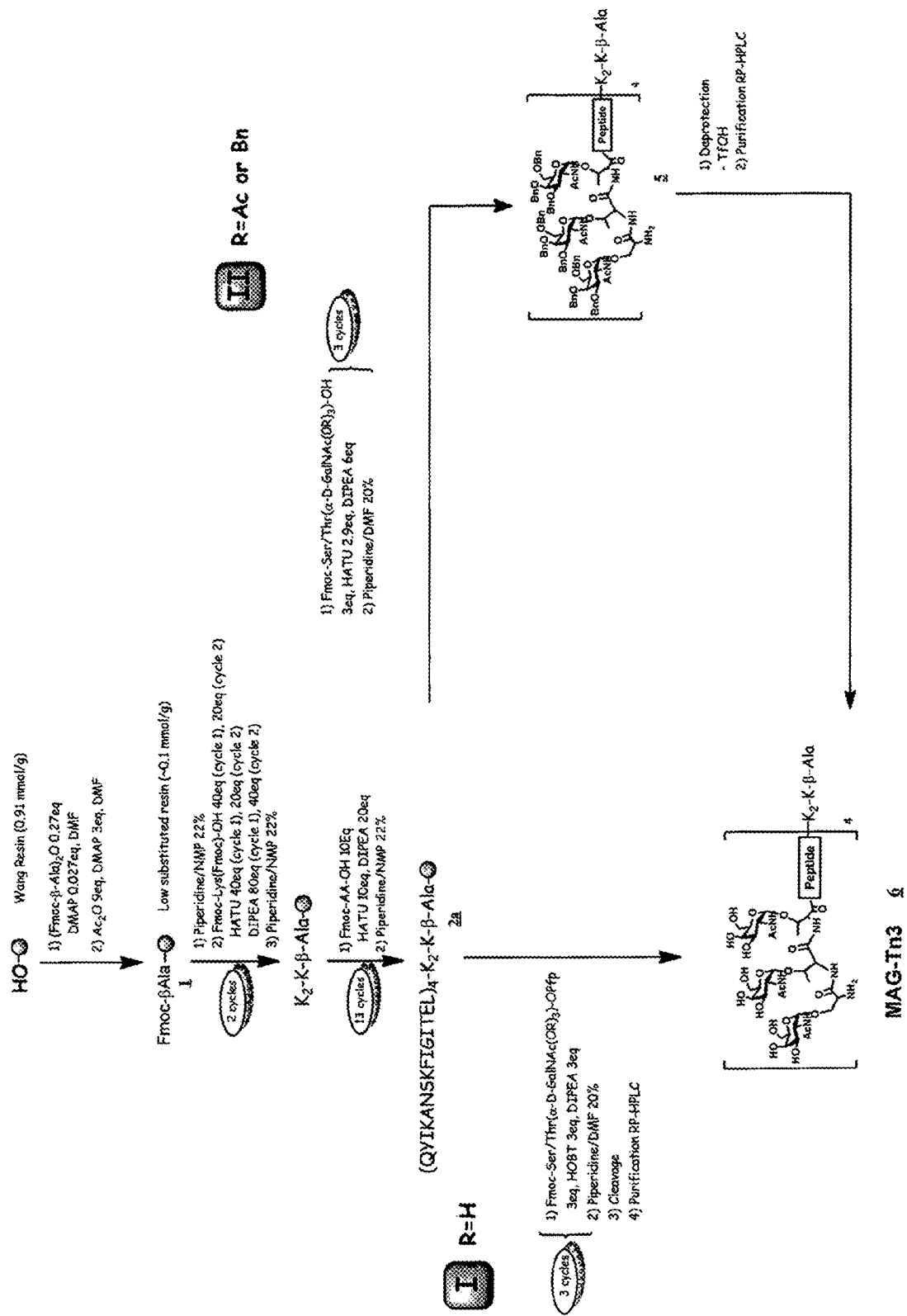

Specification includes a Sequence Listing.

(56) References Cited

OTHER PUBLICATIONS

Posnett et al., A novel method for producing anti-peptide antibodies. Production of site-specific antibodies to the T cell antigen receptor beta-chain. J Biol Chem. Feb. 5, 1988;263(4):1719-25.

Tam, Synthetic peptide vaccine design: synthesis and properties of a high-density multiple antigenic peptide system. Proc Natl Acad Sci U S A. Aug. 1988;85(15):5409-13.

Tan et al., Toward homogeneous erythropoietin: non-NCL-based chemical synthesis of the Gln78-Arg166 glycopeptide domain. J Am Chem Soc. Apr. 22, 2009;131(15):5424-31. doi: 10.1021/ja808704m.

Vichier-Guerre et al., Short synthetic glycopeptides successfully induce antibody responses to carcinoma-associated Tn antigen. J Pept Res. Feb. 2000;55(2):173-80.

* cited by examiner

METHOD FOR PREPARING MULTIPLE ANTIGEN GLYCOPEPTIDE CARBOHYDRATE CONJUGATES

This application is a continuation application of U.S. application Ser. No. 14/005,336, entitled "METHOD FOR PREPARING MULTIPLE ANTIGEN GLYCOPEPTIDE CARBOHYDRATE CONJUGATES" filed on Mar. 6, 2014 which is a national stage filing under U.S.C. § 371 of PCT International application PCT/IB2012/051285, filed Mar. 16, 2012. Application PCT/M2012/051285 claims priority under 35 U.S.C. § 119(a)-(d) or 35 U.S.C. § 365(b) of European application number 11290138.4, filed Mar. 17, 2011, entitled "METHODS FOR PREPARING MULTIPLE ANTIGEN GLYCOPEPTIDE CARBOHYDRATE CONJUGATES", which are herein incorporated by reference in their entirety.

The present invention relates to a method for preparing carbohydrate T cell epitope conjugates of formula (I), and to carbohydrate T cell epitope intermediates of formula (II) useful according to said method.

During the last decade, the MAG-Tn3, a new type of synthetic immunogen which displays the tumor-associated Tn antigen, has been developed. The MAG-Tn3 is a fully synthetic glycopeptide (MW=10,897 Da) which associates the carbohydrate Tn antigen (as a tri-Tn cluster) to a peptidic $CD4^+$ T cell epitope on a tetravalent backbone [5, 9].

MAG-Tn3 corresponds to the following structure [S(α-D-GalNAc)-T(α-D-GalNAc)-T(α-D-GalNAc)-QY$^5$IKANS$^{10}$KFIG$^{15}$TEL]$_4$-K$_2$-K-β-Ala:

Based on successful in vivo results obtained in mice and primates [8, 9], the MAG-Tn3 is a good therapeutic vaccine candidate to treat carcinomas that should advance into a phase I/II clinical trial.

A synthetic route for preparing peptide carbohydrate conjugates, such as notably MAG-Tn3 has been disclosed in the International Patent Application WO 98/43677 and in the U.S. Pat. No. 6,676,946. In this process, implemented in small-scale (1-10 mg of fmal compound), the carbohydrate Tn3 antigen is incorporated to the dendrimeric peptide M(T)$_4$ building block. It is to be noted that the incorporation of the Tn3 antigen is achieved with the fully unprotected sugar, which may appear as advantageous since it avoids a final deprotection step.

However, the inventors have shown that such a method fails when scaled-up. Indeed, the extra-incorporation of Tn residues is difficult to control and affects the crude purity and the overall yield. Further, the purification of such high molecular weight glycopeptide is complex.

Thus, there is a need for an improved method for preparing MAG-Tn3 which overcomes the drawbacks of the prior art, in particular allows to obtain better yields and purity, notably at a larger scale and in a repeatable manner.

Thus, the present invention, in one aspect, provides a novel process for preparing MAG-Tn3, and more generally carbohydrate T cell epitope conjugates of formula (I) (M(T-B)$_n$), allowing a large-scale production, with better yields and purity:

$$nB_{Pr}+M(T)_n \rightarrow M(T-B_{Pr})_n, (II) \rightarrow M(T-B)_n \qquad (I)$$

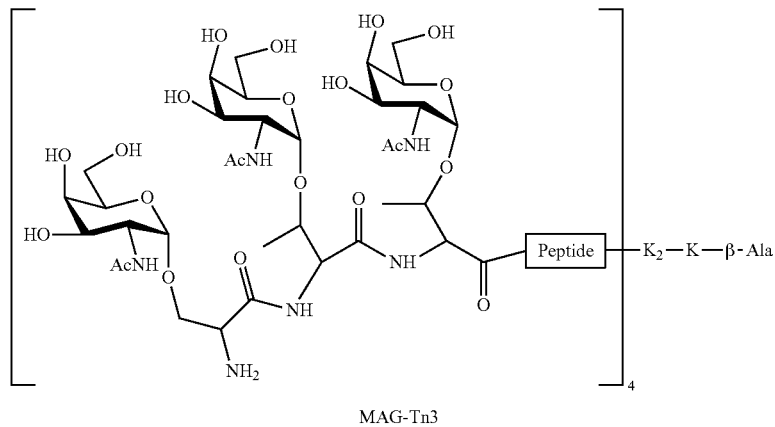

MAG-Tn3

MAG refers to Multiple Antigen Glycopeptide.

Thus, MAG-Tn3 corresponds to a carbohydrate peptide conjugate B4-T4-M of the following formula:

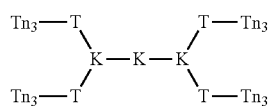

Wherein
KKK is the dendritic polyLysine core (M),
T is the peptidic $CD4^+$ T cell epitope having the following sequence: QYIKANSKFIGITEL
Tn3 is the tri-Tn B cell epitope having the following sequence: (α-GallNAc)Ser-(α-GalNAc)Thr-(α-GalNAc)Thr.

The method according to the invention advantageously enables to minimize the synthesis side-products, to improve the robustness of the process, and to scale-up the synthesis in a repeatable manner.

More specifically, it has been discovered that protecting the hydroxyl groups of the carbohydrate B cell epitope with a suitable protecting group (Pr), before incorporating the B cell epitope to the M(T)$_n$ building block, enables a better control of the B cell epitope incorporation, and thus to improve both the yields and purity, in particular at a large scale.

Another object of the present invention is to provide novel carbohydrate T cell epitope conjugates of formula (II) (M(T-B$_{Pr}$)$_n$), which compounds are useful for the preparation of carbohydrate T cell epitope conjugates of formula M(T-B)$_n$ with high yields and purity.

A further object of the present invention is to provide carbohydrate T cell epitope conjugates of formula (I) (M(T-B)$_n$) having a purity grade superior than 95%, obtainable by the process according to the invention.

These and other objects, features and advantages of the method according to the invention will be disclosed in the following detailed description of the patent disclosure.

Thus, in one aspect, the present invention relates to a method for preparing a carbohydrate T cell epitope conjugate of formula (I):

$$M(T-B)_n \quad (I)$$

wherein:

M is a dendrimeric poly-Lysine core;

T is a T cell epitope comprising a peptide;

B is a carbohydrate B cell epitope comprising at least one carbohydrate residue (b);

n is an integer and represents the number of -T-B groups covalently bonded to M;

Said method comprising the steps of:

i) coupling a protected carbohydrate B cell epitope (B$_{Pr}$) which hydroxyl groups of the carbohydrate residue (b) are protected with a protecting group (Pr), with a compound M(T)$_n$ thereby forming a carbohydrate T cell epitope conjugate M(T-B$_{Pr}$)$_n$, said protecting group (Pr) being selected from the group consisting of allyl, p-methoxybenzyl (PMB), t-butyldimethylsilyl (TBDMS), benzyloxymethyl (BOM), levulinyl (Lev), benzoyl (Bz), 2,5-difluorobenzoyl, chloroacetyl, benzyl (Bn) or an acetyl (Ac), or forming with two hydroxyl groups to which it is attached a C$_5$-C$_6$ isopropylidene ketal or a C$_5$-C$_6$ cyclic alkylcarbonate; and ii) removing the protecting groups Pr from the obtained conjugate M(T-B$_{Pr}$)$_n$ thereby obtaining the carbohydrate T cell epitope conjugate M(T-B)$_n$.

Dendrimeric poly-Lysine core (M)

The poly-Lysine core of the conjugate of formula (I) is a dendrimeric structure, which may be represented as a star, having multiple branches (-T-B), which may be identical or not.

Such branches are covalently bonded to the NH$_2$ end of each lysine residue of the dendrimeric core, notably by a peptide bond —NH—C(=O)—.

The valence m of the dendrimeric polyLysine core (M), i.e the number of NH$_2$ end of each lysine residue is such that m≥n, preferably m=n, n designating the number of (-T-B) branches covalently bonded to M.

In another aspect, the number of (-T-B) branches n ranges from 4 to 16, notably from 4 to 8.

In a further aspect, the dendrimeric polyLysine core M comprises at least 3 lysine residues, in particular 3 to 15 lysine residues, more particularly 3 to 7 lysine residues.

In an additional aspect, the conjugate M(T-B)$_n$ is selected from the following formulae (Ia) or (Ib):

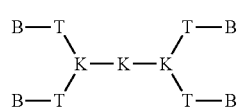

(Ia)

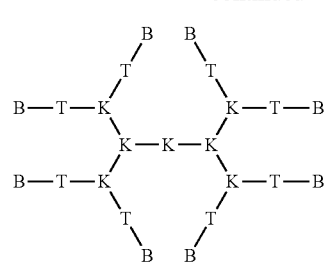

(Ib)

wherein:

K is a lysine residue, and T and B are as defined above.

Advantageously, dendrimeric structures (Ia) and (Ib) provide a high density of antigens at the surface of the dendrimeric polyLysine core M.

In a further aspect, M is (K)$_2$K-βAla-OH of the following formula:

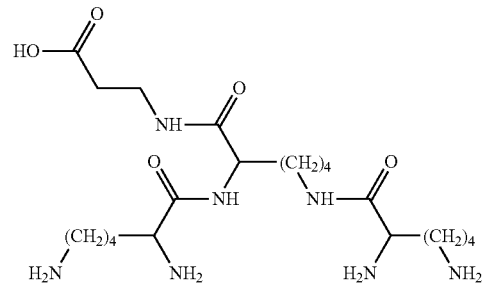

(T-B) Branches

The presence of both carbohydrate B cell epitopes and T cell epitopes on the conjugate of formula (I) renders the latter an efficient immunogen.

T Cell Epitopes

As used herein, T cell epitope means an antigen, in particular of a peptidic nature, capable of eliciting a T cell response.

Such epitopes are notably described in S. Stevanovic, "*Identification of Tumour-associated T-cell epitopes for vaccine development*", Nature Reviews, Vol. 2, July 2002, p. 1 to 7; J. H. Kessler, C. J. M. Melief, "*Identification of T-cell epitopes for cancer immunotherapy*", Leukemia (2007) 21, 1859-1874, or in the Cancer immunity/peptide database website: http://www.cancerimmunity.org/peptide database/ tumorspecific.htm.

The T cell epitopes incorporated in the conjugate of formula (I) may be the same or different, peptidic or not.

In a particular aspect, carbohydrate T cell epitope conjugates are carbohydrate peptide conjugates. Peptidic T-cell epitopes can comprise 2 to 50 amino-acids.

T cell epitopes may notably be selected amongst CD8$^+$, or CD4$^+$ T cell epitopes.

CD8$^+$ T cell epitopes, recognized as tumoral markers, may be selected from the group consisting of:

MUC-1 peptides (pancreas, breast)

MAGE 1 and 3 (melanoma, lung) (T. Boon et al. (1995), Immunology Today, vol. 16 no 7, pp 334-336)

pme117/gp 100 (melanoma)

Tyrosinase (melanoma) BAGE (melanoma)

GAGE (melanoma) LB-33-B (melanoma)

CDK4 p185$^{HER}$ (breast, ovary)

CEA MARTI/Melan-A (melanoma)
or selected in the group consisting of tumor antigens described in A. Van Pel et al. (1995) Immunological. Reviews no 145, pp 229-250 or in P. G. Coulie (1995), Stem Cells, 13, pp 393-403.

In a particular aspect, T is or comprises a CD4$^+$ T cell epitope, which may be notably a poliovirus (PV) protein fragment, a tetanus toxin fragment or a PADRE peptide.

As an example of CD4$^+$ T cell epitope selected amongst poliovirus (PV) protein fragment, mention may be made of the synthetic peptide that corresponds to the 103-115 sequence of VP1 protein from poliovirus type 1 (KL-FAVWKITYKDT) (SEQ ID No 4).

As example of CD4$^+$ T cell epitope selected amongst tetanus toxin fragment, mention may be made of the following fragments:
  830-844 sequence of the tetanus toxin (QYIKANSKFIGI-TEL) (SEQ ID No 1)
  947-967 sequence of the tetanus toxin (FNNFTVSFWLRVPKVSASHLE) (SEQ ID No 2)
  1273-1284 sequence of the tetanus toxin (GQIGND-PNRDIL) (SEQ ID No 3).

These peptidic T cell epitopes typically bind to a plurality of MHC (Major Histocompatibility Complex) human and murine molecules of class II avoiding in consequence the restriction problems encountered with the CD4+ T cellular response, associated with the polymorphism of the MHC molecules existing between individuals. Moreover the use of tetanus toxin peptides should increase the immunogenicity of antigens present on the conjugate of the present invention, as a result of the vaccination of numerous individuals with the tetanus toxoid.

As further examples of peptide T-cell epitopes, reference may be made to S. Stevanovic, "*Identification of Tumour-associated T-cell epitopes for vaccine development*", Nature Reviews, Vol. 2, July 2002, p. 1 to 7; J. H. Kessler, C. J. M. Melief, "*Identification of T-cell epitopes for cancer immunotherapy*", Leukemia (2007) 21, 1859-1874, or in the Cancer immunity/peptide database website: http://www.cancerimmunity.org/peptide database/tumorspecific.htm.

Examples of non-peptidic T cell epitopes include notably:
  fragments of pneumococcal type 4 polysaccharide, and oligosaccharide tetanus toxoid conjugates as described by C. C. A. M. Peeters (1991), in The Journal of Immunology, 146, 4309-4314,
  meningococcal liposaccharides as described by A. F. M. Verheul (1991) in Detection and Immunity, vol. 59, no 10, pp. 3566-3573.

B Cell Epitopes

As used herein, B cell epitope means antigens capable of eliciting a B cell response.

As used herein, a carbohydrate means a saccharide, notably mono-, di-, oligo-, and polysaccharides.

In a preferred aspect, the carbohydrate residue (b) forming the B cell epitope of the conjugate of formula (I) is a N-acetylgalactopyranosyl residue, or a derivative thereof.

In a particular aspect, the carbohydrate residue (b) is attached to an amino acid, peptide, or lipid residue. In yet a further aspect, the carbohydrate residue is an O-glycosyl amino acid or peptide. In a further aspect, the B cell epitope is attached to the dendrimeric structure $M(T)_n$ via said aminoacid or peptide.

The B cell epitope may comprise one or more carbohydrate residues (b), notably 1 to 10, in particular 1 to 6 carbohydrate residues.

Such B cell epitope may be selected from tumor (cancer) glycosidic antigens, notably from:

the glycolipid class, including acidic glycolipid such as, for example, gangliosides GD2, GD3 and GM3 (melanoma) and neutral glycolipids such as, for example, the Lewisy (Ley) (breast, prostate, ovary) and the Globo H (breast, prostate, ovary) antigens;

the O-glycosyl peptides (or aminoacid) class such as, for example, the Tn antigen (α-GalNAc-Ser or α-GalNAc-Thr), TF antigen (β-Gal-(1-3)-α-GalNAc-Ser or β-Gal-(1-3)-α-GalNAc-Thr), two tumor markers frequently present in carcinomas but not usually in normal tissues [Springer G. F. Science 224, 1198-1206 (1984)] (ovary, breast, lung), or di-Tn (α-GalNAc-Ser/Thr)$_2$, tri-Tn (α-GalNAc-Ser/Thr)$_3$ or hexa-Tn (α-GalNAc-Ser/Thr)$_6$ The B cell epitope of the conjugate according to the present invention may also originate from capsular bacterial polysaccharides of, for example, *Neisseria meningitis, Haemophilus influenzae, Streptococcus pneumoniae*, and of the *Streptococcus* group.

The polysaccharides are carbohydrate residues obtained by a synthetic process.

The B cell epitope of the present conjugate may be also of fungal origin, such as for example, one isolated from the yeast *Saccharomyces*.

In a preferred aspect, the B cell epitopes of the conjugate of formula (I) are preferentially tumor markers, such as, for example, Tn and TF antigens.

It can be selected from the group comprising Tn, di-Tn, tri-Tn (Tn3), hexa-Tn (Tn6), or TF antigens.

In a further aspect, B is or comprises the carbohydrate residues selected from the group consisting of:
  α-GalNAc,
  α-GalNAc-Ser,
  α-GalNAc-Thr,
  β-GalNAc,
  β-GalNAc-Ser,
  β-GalNAc-Thr,
  β-Gal-(1-3)-α-GalNAc-Ser,
  β-Gal-(1-3)α-GalNAc-Thr,
  (α-GalNAc-Ser/Thr)$_2$,
  (α-GalNAc-Ser/Thr)$_3$, and
  (α-GalNAc-Ser/Thr)$_6$, In a preferred aspect, B is or comprises the residue (α-GalNAc-Ser/Thr)$_3$, most preferably (α-GalNAc)Ser-(α-GalNAc)Thr-(α-GalNAc)Thr.

In another preferred embodiment, the conjugate of formula (I) is MAG-Tn3.

Step i)

The method according to the present invention, comprises the step i) of coupling a protected carbohydrate B cell epitope ($B_{Pr}$) which hydroxyl groups of the carbohydrate residue (b) are protected with a protecting group (Pr), with a compound $M(T)_n$ thereby forming a carbohydrate T cell epitope conjugate $M(T-B_{Pr})_n$, said protecting group (Pr) being selected from the group consisting of allyl, p-methoxybenzyl (PMB), t-butyldimethylsilyl (TBDMS), benzyloxymethyl (BOM), levulinyl (Lev), benzoyl (Bz), 2,5-difluorobenzoyl, chloroacetyl, benzyl (Bn) or an acetyl (Ac), or forming with two hydroxyl groups to which it is attached a $C_5$-$C_6$ isopropylidene ketal or a $C_5$-$C_6$ cyclic alkylcarbonate.

In a preferred aspect, Pr is benzyl (Bn) or acetyl (Ac).

In a particular aspect, step i) comprises the steps of:

a) Coupling a first protected carbohydrate residue ($b_{Pr}$) which hydroxyl groups are protected with a protecting group (Pr), notably selected from benzyl (Bn) or acetyl (Ac), with a compound M(T)$_n$ thereby forming a carbohydrate T cell epitope conjugate M(T-b$_{Pr}$)$_n$; and optionally.

b) repeating step a) with further protected carbohydrate residues (b$_{Pr}$) up to obtaining a protected carbohydrate conjugate of formula (II) M(T-B$_{Pr}$)$_n$.

Advantageously, it has been demonstrated that such protecting groups Pr enable to control the coupling of each of the carbohydrate residues b, or of the B cell epitope B, with M(T)$_n$ in step i). Further, it has been shown that the removal of these protecting groups allows to obtain the desired product, with an improved compromise between yield and purity.

The hydroxyl groups of the carbohydrate residue can be protected by the above mentioned protecting groups (Pr), notably by benzyl or acetyl groups, according to conventional methods.

Protected B cell epitopes B$_{Pr}$ or carbohydrate residues (b$_{Pr}$) may be commercially available or may be prepared from commercially available starting materials and/or according to conventional methods.

In a preferred aspect, the dendrimeric polyLysine core M and thus the subsequent M(T)$_n$ building block are immobilized on a solid support, thus enabling iterative solid phase peptide synthesis.

As an example of solid support, mention may be made of a polystyrene resin functionalized with p-benzyloxybenzyl alcohol (Wang resin) on which Fmoc-β-Ala-groups may then be grafted or those sold under the trade name Fmoc-β-Ala-TentaGel R Trt. The M core may notably be attached via a β-Ala-OH residue. The resin substitution ratio, ie the grafting ratio of the resin by Fmoc-β-Ala-groups may range from 0.2 to 0.05 mmol/g, preferably from 0.10 to 0.13 mmol/g.

In a particular aspect, b$_{Pr}$ is a protected O-glycosyl amino acid or peptide. Protected O-glycosyl peptide may be coupled to the M(T)$_n$ building block by successively introducing the protected constitutive O-glycosyl amino acid residues b$_{Pr}$.

In this regard, the solid phase peptide and glycopeptide synthesis may be performed using the standard Frnoc chemistry protocol [51] and [6]. N-α-Fmoc aminoacids and glycosylated aminoacids or peptides are incorporated stepwise in the peptide chain.

Thus, step i) may be performed by reacting a first protected N-α-Fmoc O-glycosyl amino acid b$_{Pr}$ with the M(T)$_n$ building block. More specifically, the carboxylic group (COOH) of the first O-glycosyl amino acid b$_{Pr}$ is reacted with the NH$_2$ end of each of the T branches, thereby forming a peptide covalent bond (—C(=O)NH—).

The Fmoc is cleaved, for example in the presence of 20% of piperidine in DMF or NMP. Then a second protected N-α-Fmoc O-glycosyl amino acid b$_{Pr}$ may be similarly reacted with the NH$_2$ group of the first protected amino acid residue, and so on.

Thus, when the B cell epitope comprises several carbohydrate residues (b), step i) of the method according to the invention may comprise the step of repeating the coupling according to step a) up to obtaining the carbohydrate T cell epitope conjugate M(T-B$_{Pr}$)$_n$.

These peptide coupling may be carried out in a polar aprotic solvent such as DMF or NMP, in the presence of coupling reagents such as HATU and DIPEA or DIC/HOBt, and PyBOP.

Step ii)

In a particular aspect, Pr is benzyl. In that case, the deprotection step ii) may be carried out in the presence of TfOH or by a catalytic hydrogenation.

In a particular aspect, step ii) is a catalytic hydrogenation.

In a preferred aspect, the catalytic hydrogenation is carried out in the presence of Pd/C, notably of 10% Pd/C (% w/w), as a catalyst. The weight ratio of the conjugate of formula (II)/catalyst may vary from 10/2 to 10/10, and is preferably of about 10/8. The catalyst may be added portionwise over a long period.

The catalytic hydrogenation is preferably carried out in NMP/H$_2$O, notably in a volume ratio of 87.5/12.5, as a solvent.

The catalytic hydrogenation reaction is preferably carried out at a temperature ranging from 20 to 40° C., in particular at about 37° C.

The catalytic hydrogenation reaction is preferably carried out under a pressure ranging from 1 to 10 bar, more preferably at about 5 bar.

In another aspect, step ii) is carried out in the presence of TfOH.

Preferably, the conjugate of formula (II) is reacted with TfOH, in the presence of TFA, DMS and m-cresol. The relative ratio of TfOH/TFA/DMF/m-cresol may be of 1/5/3/1 v/v/v/v.

In another aspect, the protecting group Pr is acetyl.

The deprotection of acetyl protecting groups in step ii) is preferably performed in the presence of hydrazine, in a protic polar solvent, for example an alcohol such as methanol. This reaction may be performed at room temperature, i.e. between 15 and 25° C.

The molar ratio of hydrazine relative to the compound of formula (II) may vary from 100 to 1500 molar equivalents.

The deprotection of acetyl may alternatively be performed in the presence of MeONa, notably in MeOH as a solvent, at room temperature, i.e. between 15 and 25° C.

In a particular aspect, when immobilized in a solid support, the conjugate of formula (II) obtained at the end of i) is preliminary cleaved from the solid support, before performing the deprotection step ii). Such cleavage may be performed in the presence of TFA and TIS in water, for example with the following volume ratio 95/2.5/2.5 v/v/v.

Step iii)

The method according to the invention may further comprise a step iii) subsequent to step ii) consisting in one or more purification steps, notably by reverse phase high-performance liquid chromatography (RP-HPLC).

Step iv)

The method according to the invention may further comprise a subsequent step iv) of recovering the product.

M(T)$_n$ Synthesis

In a particular aspect, the method according to the invention further comprises the step of preparing the conjugate M(T)$_n$.

In a particular embodiment, the conjugate M(T)$_n$ is prepared starting from the dendrimeric polyLysine core and by introducing stepwise the N-protected amino acid residues constituting the peptide T cell epitope. The N-protected amino acid residues are notably Fmoc amino acid residues.

The amino acid couplings may be performed in a polar aprotic solvent such as DMF, in the presence of one or more peptide coupling reagents such as DIC, HOBt, PyBOP, HAM or DIPEA. The combinations (DIC/HOBt and PyBOP) or alternatively (HATU/DIPEA) are particularly preferred. Alternative coupling reagents are also disclosed in E. Valeur; M. Bradley, Chem Soc Rev (2009) 38, 606; A. El-Faham et al. Chem Eur J (2009) 15, 9404 or R. Subiros-Funosas et al. Org Biomol Chem (2010) 8, 3665.

Following each peptide coupling, the N-amino acid protecting groups are removed. As an example, Fmoc protecting groups can be removed in the presence of piperidine in a polar aprotic solvent such as DMF.

As regards the synthesis of the peptide fragment SEQ ID no1 the amino acid residues $AA^{9-10}$ and $AA^{15-16}$ can be incorporated as pseudo-proline dipeptides. Advantageously, the incorporation of such dipeptides demonstrated a significant impact on the crude quality of the product.

M Synthesis

In a particular aspect, the method according to the invention further comprises the step of preparing a dendrimeric polyLysine core M.

The dendrimeric polyLysine core M may be prepared according to the method disclosed in U.S. Pat. No. 6,676,946.

Carbohydrate T Cell Epitope Conjugate $M(T-B)_n$

In another aspect, the present invention advantageously provides a carbohydrate T cell epitope conjugate $M(T-B)_n$ having a grade of purity ≥95% obtainable according to the method of the invention.

Such a purity grade may be obtained by performing a purification step (iii) after step (ii), notably a reverse phase high-performance liquid chromatography (RP-HPLC). As an example, RP-HPLC may be performed with a low-granulometry column, notably having a granulometry inferior to 15 µm, notably of about 10 µm or inferior to 5µ and/or having a pore size of about 300 Å or less, notably less than 200 Å, in particular less than 100 Å. The stationary phase may be a reversed phase based on silica gel grafted by octadecyl groups (also called C18 silica). Elution may be performed with water (0.1% TFA)/acetonitrile with a shallow gradient, for instance from 70/30 to 60/40 over a period of about 20 minutes.

The purity grade of the conjugate of formula (I) can be determined by any conventional method, notably by RP-HPLC.

The purity is preferably ≥96%, notably ≥98%, and advantageously ≥99%.

Carbohydrate T Cell Epitope Conjugate $M(T-B_{Pr})_n$

In an additional aspect, the present invention provides a carbohydrate T cell epitope conjugate of formula (II):

$$M(T-B_{Pr})_n \quad (II)$$

Wherein

M is a dendrimeric poly-Lysine core;

T is a T cell epitope, preferably comprising a peptide residue;

$B_{Pr}$ is a protected carbohydrate B cell epitope comprising at least one carbohydrate residue (b) which hydroxyl groups are protected by a Pr group,
  said Pr group being selected from the group consisting of allyl, p-methoxybenzyl (PMB), t-butyldimethylsilyl (TBDMS), benzyloxymethyl (BOM), levulinyl (Lev), benzoyl (Bz), 2,5-difluorobenzoyl, chloroacetyl, benzyl (Bn) or an acetyl (Ac),
  or forming with two hydroxyl groups to which it is attached a $C_5$-$C_6$ isopropylidene ketal or a $C_5$-$C_6$ cyclic alkylcarbonate and n is an integer and represents the number of -T-B groups covalently bonded to M.

In a particular aspect, $B_{Pr}$ is a protected (α-GalNAc-Ser/Thr)3.

In an additional aspect, Pr is benzyl or acetyl

In a further aspect, M is HO-βAla-K(K)$_2$.

In another aspect, T is QYIKANSKFIGITEL (SEQ ID No 1).

In another object, the invention provides a use of a carbohydrate peptide conjugate $M(T-B_{Pr})_n$ for preparing a carbohydrate peptide conjugate $M(T-B)_n$, $M(T-B_{Pr})_n$ and $M(T-B)_n$ being as defined above.

Other features of the invention will become apparent in the course of the following descriptions of exemplary embodiments. These examples are given for illustration of the invention and are not intended to be limiting thereof.

FIGURES

FIG. 1: MAG-Tn3 synthesis according to protocol A of the method of the invention. The molar equivalents are indicated relative to amino group. The $AA^{9-10}$ and $AA^{15-16}$ are incorporated as pseudo-Pro dipeptides.

Figure 2:
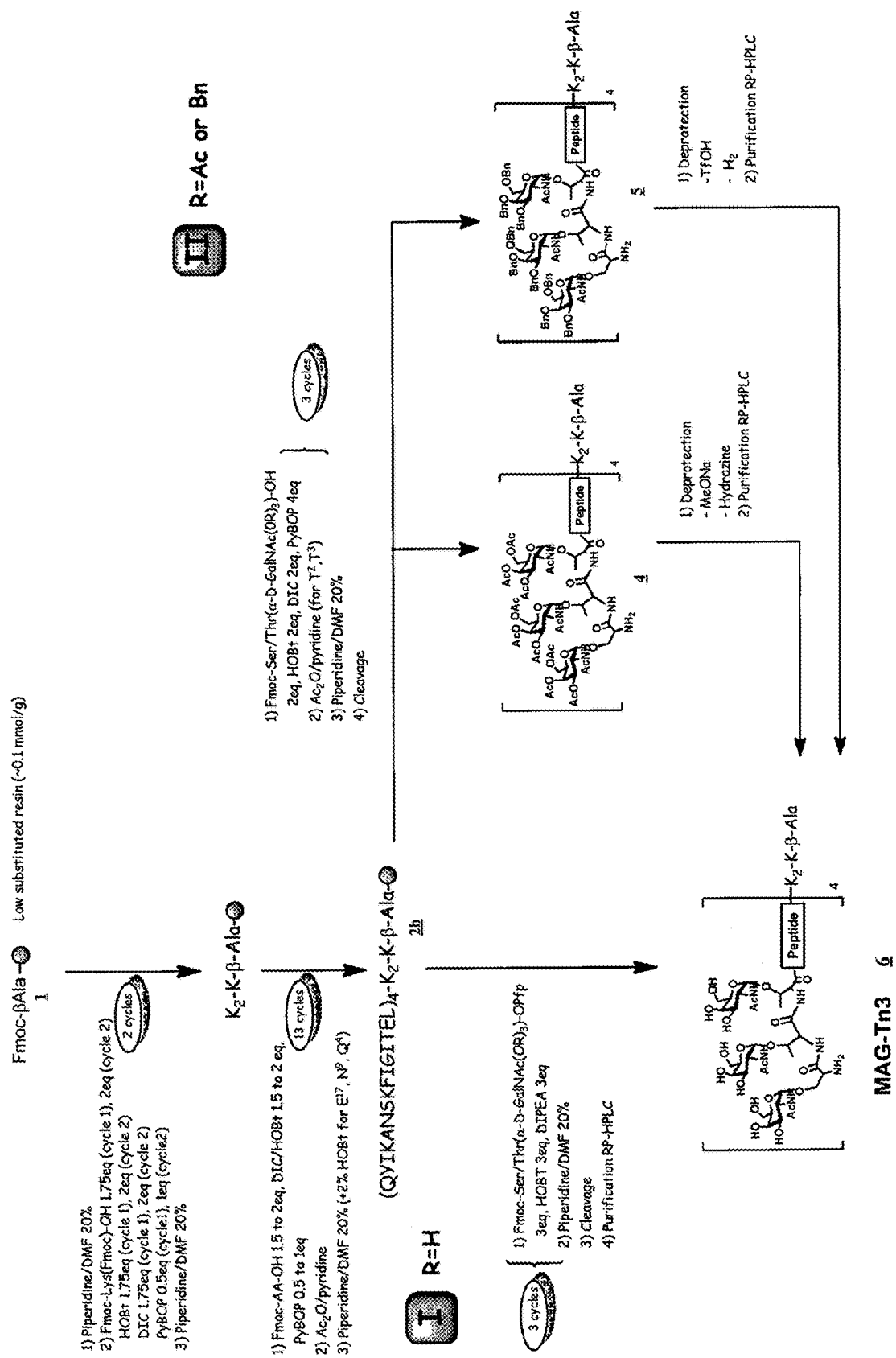

FIG. 2: MAG-Tn3 synthesis according to protocol B of the method of the invention. The molar equivalents are indicated relative to amino group. The $AA^{9-10}$ and $AA^{15-16}$ are incorporated as pseudo-Pro dipeptides.

ABBREVIATIONS

AA amino acid

Ac acetyl

AcOH acetic acid

Bn benzyl

Boc tert-butoxycarbonyl tBu tert-butyl

DIC N,N'-diisopropylcarbodiimide

DIPEA diisopropylethylamine

DIPE diisopropyl ether

DMAP 4-dimethylaminopyridine

DMF dimethylformamide

DMS dimethylsulfide

DVB divinylbenzene

EtOH ethanol

FA formic acid

Fmoc 9-fluorenylmethoxycarbonyl

HATU 2-(1H-9-azabenzotriazole-1-yl)-1,1,3,3-tetramethyluronium hexafluorophosphate HOBt N-hydroxybenzotriazole HPLC/MS high performance liquid chromatography/mass spectroscopy MAG multiple antigenic glycoppeptide MeOH methanol MeONa sodium methylate ESMS electrospray mass spectrometry MW molecular weight NMP N-methylpyrrolidone NMR nuclear magnetic resonance PyBOP benzotriazole-1-yl-oxy-tris-pyrrolidino-phosphonium hexafluorophosphate RP-HPLC reverse phase high-performance liquid chromatography RT room temperature SELDI-TOF MS surface-enhanced laser desorption/ionization time-of-flight mass spectrometry TBS tert-butyldimethylsilyl TFA trifluoroacetic acid TfOH trifluoromethanesulfonic acid THF tetrahydrofuran TIS triisopropylsilane TMSBr trimethylsilyl bromide Trt trityl

EXAMPLES

Example 1: Preparation of MAG-Tn3 Via Protocol A and B

General Methods

The synthesis of 6 was performed stepwise on solid-phase using Fmoc chemistry. Amino acid side chain protective groups used were Trt on Gln and Asn, Boc on the Lys[7] and Lys[11], tBu on Tyr, Ser and Thr, OtBu on Glu. For the Lys[19] and Lys[20], the protective groups were Fmoc.

The net peptide contents were determined by nitrogen analysis or quantitative amino acid analysis using a Beckman 6300 analyser after hydrolysis of the compounds with 6N HCl at 110° C. for 20 h.

The HPLC/MS analyses were performed on an Alliance 2695 system coupled to a UV detector 2487 (220 nm) and to a Q-Tofinicro™ spectrometer (Micromass) with an electrospray ionisation (positive mode) source (Waters). The samples were cooled to 4° C. on the autosampler. The linear gradient was performed with acetonitrile+0.025% FA (A)/ water+0.04% TFA+0.05% FA (B) over 20 min. The column was a Zorbax 300SB C18 (3.5µ, 3×150 mm) (Agilent) (gradient 13-53% A) or a XBridge™ BEH130 C18 (3.5µ, 2.1×150 mm) (Waters) (gradient 15-40% A). The temperature of the source was maintained at 120° C. and the desolvation temperature at 400° C. The cone voltage was 40V.

The ESMS analyses were recorded in the positive mode by direct infusion in the same mass spectrometer. The samples were dissolved at ~5 µM concentration in water/ acetonitrile (1/1) with 0.1% formic acid.

The SELDI-TOF analyses were performed on a PCS 4000 mass spectrometer (Bio-Rad Labs). H4 ProteinChip array surfaces were activated with 1 µL $CH_3CN$. Spots were incubated with the reaction mixture (2.5 µL, 1 mg/mL) in a box at RT for 20 min. They were then washed with the reaction buffer (3×1 min) and $H_2O$ (3×1 min). The matrix (2×0.6 µL of sinapinic acid saturated in 50% $CH_3CN$/0.5% TFA) was applied on each spot and allowed to air-dry. Spectra were generated from each array spot with a laser setting ~3 µJ. The instrument was externally calibrated with bovine ubiquitin, bovine cytochrome C, β-lactoglobulin with the matrix and the settings as described above.

The purity of 6 was analyzed by RP-HPLC using an Agilent 1200 pump system with a UV detector at 220 nm. The column was a Zorbax 300SB C18 (3.5µ, 3×150 mm) (Agilent) and the gradient was performed with acetonitrile+ 0.1% TFA (A)/water+0.1% TFA (B) over 40 min, from 13 to 53% A (0.8 mL/min, retention time 20.5 min).

The molar equivalents of all reagents are indicated relative to amino groups. The molar amounts of the protected intermediates 4 and 5 are calculated based on the starting Fmoc-β-Ala-resin 1 substitution. The overall yields (Table) include all the synthetic steps from 1. They were calculated on the net peptide content of the final product 6 from the Fmoc-β-Ala-resin 1 substitution.

Protocol A (FIG. 1)

Fmoc-β-Ala-Resin (Low-Substituted Resin) 1

2 g of p-benzyloxybenzyl alcohol resin (Wang resin, 0.91 mmol/g, 100-200 mesh, polymer matrix: copoly(styrene-1% DVB), Novabiochem) were swelled in DMF (Applied Biosystems) for 1 h in a dry round-bottomed flask. 311 mg (1 mmol) of dry Fmoc-β-Ala-OH (Novabiochem, Merck Chemicals Ltd) were dissolved in 8 mL of anhydrous $CH_2Cl_2$ (Acros). Four drops of DMF were added to complete the dissolution. After the addition of 77 µL (0.5 mmol) of DIC (Fluka), the reaction mixture was stirred for 20 min under argon, at room temperature. The reaction mixture was evaporated to dryness and the rotary evaporator opened under argon. The residue was dissolved in the minimum volume of DMF (6 mL) and the solution was added to the resin. 6 mg (0.05 mmol) of DMAP (Acros) dissolved in 0.5 mL of DMF were added and the suspension was stirred gently for 2 h at room temperature.

The resin substitution rate was measured by UV analysis of a resin sample according to the following procedure. 2 to 6 mg of resin were transferred with a Pasteur pipette to a small sintered glass furmel. The resin was washed with DMF, $CH_2Cl_2$ (Carlo Erba) and dried. The resin was transferred in an UV cell, precisely weighted and then added with 2.8 mL of 20% piperidine (Aldrich) in DMF. The suspension was agitated with the aid of a Pasteur pipette for 2 min. The absorbance was read at 300.5 nm (ε=7800) with the reference cell containing 20% piperidine in DMF. The extent of loading was found to be 0.1 mmol/g.

The resin was washed three times with DMF. The residual hydroxyl groups were capped using the following protocol. The resin was resuspended in 13 mL of DMF. 1.55 mL (16.4 mmol) of $Ac_2O$ (Sigma) in 1 mL of DMF, and then 660 mg (5.41 mmol) of DMAP in 1 mL of DMF were added. After gently stirring for 30 min at room temperature, the suspension was filtered in a sintered glass funnel, successively washed three times by DMF, three times by $CH_2Cl_2$ and then was dried overnight in a desiccator. The resin 1 was stored at 4° C.

[QYIKANSKFIGITEL]$_4$-K$_2$-K-β-Ala-Resin (protected peptide) 2

The tetravalent peptide was synthesized from 250 mg (25 µmol) of Fmoc-β-Ala-resin 1 on an Applied Biosystems peptide synthesizer 433A using Fmoc chemistry. The Applied standard synthesis protocol was followed except for an additional washing step after each coupling step. Briefly, the Fmoc groups were removed with 22% piperidine in NMP (Applied Biosystems) and the deprotection was monitored by conductivity. The lysine core was constructed by successively coupling two levels of Fmoc-Lys(Fmoc)-OH (Applied Biosystems) (1$^{st}$ cycle: 40eq, 2$^{nd}$ cycle: 20eq) using HATU (Applied Biosystems) (1$^{st}$ cycle: 40eq, 2$^{nd}$ cycle 20eq)/DIPEA (Applied Biosystems) (1$^{st}$ cycle 80eq, 2$^{nd}$ cycle: 40eq) as the coupling reagents and NMP as solvent (Note: the use of this very large excess of reagents should be not necessary for the efficiency of the reaction and is only due to the fact that the prepacked cartridges are filled with 1mmol of amino acid). The stepwise introduction of the subsequent Fmoc-protected amino acids (Applied Biosystems, 10eq/amine) carrying standard side-chain protective groups was performed with HATU (10eq/amine)/DIPEA (20eq/amine) in NMP. The AA in positions 15-16 and 9-10 were incorporated as, respectively, Fmoc-Ile-Thr($\Psi^{Me,Me}$pro)-OH and F/inoc-Asn(Trt)-Ser($\Psi^{Me,Me}$pro)-OH (10eq/ amine) (Novabiochem, Merck Chemicals Ltd) with HATU (10eq/amine) and DIPEA (20eq/amine).

[S(α-D-GalNAc(OBn)$_3$)-T(α-D-GalNAc(OBn)$_3$)-T(α-D-GalNAc(OBn)$_3$)-QYIKANSKFIGITEL]$_4$-K$_2$-K-β-Ala 5

Starting from 2 (25 µmol), the glycosylated building blocks were incorporated manually: Fmoc-T(α-D-GalNAc (OBn)$_3$)-OH (Ficher Chemicals AG) (1$^{st}$ cycle), Fmoc-T(α-

D-GalNAc(OBn)$_3$)-OH (2$^{nd}$ cycle) and Fmoc-S(α-D-GalNAc(OBn)$_3$)-OH (Ficher Chemicals AG) (3$^{rd}$ cycle). Briefly, the dry building block (0.3 mmol, 3eq/free amino group) was dissolved in the minimum amount of DMF (~mL). A solution of 55 mg (0.145 mmmol) of HATU (Novabiochem) in 0.5 mL DMF was added and the resulting mixture was added to the resin. After adding 52 µL (0.3 mmol) of DIPEA (Aldrich), the suspension was mechanically stirred. The three coupling steps were monitored by the Kaiser test [1] and were completed, respectively, in 1 h, 1 h and 1 h. After each coupling steps, the resin was washed with DMF (four times). All Fmoc cleavages were carried out by treatment of the resin with 20% piperidine in DMF. Following each deprotection, the resin was successively washed by DMF (six times), CH$_2$Cl$_2$ (six times), and DMF (six times). At the end of the synthesis, the resin was extensively washed with DMF and CH$_2$Cl$_2$, and dried in a desiccator. 10 mL of TFA (Applied Biosystems)/water/TIS (Acros) (95/2.5/2.5 v/v/v) were added to the resin at 4° C. and the mixture was stirred for 1 h30 at room temperature. After filtration of the resin, the solution was concentrated and the crude product precipitated with diethyl ether. After centrifugation, the pellet was dissolved in water and lyophilized to yield 229 mg of the crude glycopeptide 5.

[S(α-D-GalNAc)-T(α-D-GalNAc)-T(α-D-GalNAc)-

QYIKANSKFIGITEL]$_4$-K$_2$-K-β-Ala or MAG-Tn3 6

From 5,

With TfOH [2-4]

200 mg (0.014 mmol) of 5 were dissolved in 2.96 mL of TFA, 1.78 mL of DMS (Sigma-Aldrich) and 587 µL of metacresol (Sigma-Aldrich) at RT. The solution was cooled to −10° C. and 587 µL, of TfOH (Fluka) was added and the mixture was stirred 1 h15 at −10° C. (TfOH/TFA/DMS/m-cresol 1/5/3/1 v/v/v/v). The product was precipitated with diethyl ether and, after centrifugation, the pellet was dissolved in water and lyophilized to yield 372 mg of the crude glycopeptide. The product was dissolved in 7.7 mL of 0.05 M ammonium acetate buffer and the pH adjusted to 7 with 1 M ammonia. After 1 h at room temperature, the solution was lyophilized to yield 412 mg of the crude product. The product was purified by RP-HPLC using an Agilent 1200 pump system with a UV detector at 230 nm. The column was a Zorbax C18 (5µ, 300 Å, 9.4×250 mm) (Agilent) and the gradient was performed with water (0.1% TFA)/acetonitrile over 20 min, from 73/27 to 60/40. The purification gave 3.9 mg (net peptide content) of 6 in 95.90% purity. The overall yield is 1.6%.

Protocol B (FIG. 2)

[QYIKANSKFIGITEL]$_4$-K$_2$-K-β-Ala-Resin (protected peptide) 2

Until the incorporation of Tyr$^5$, the tetravalent peptide was synthesized from 36.9 g (4.8 mmol) of Fmoc-β-Ala-Tentagel R Trt resin 1 (0.13 mmol/g) (Rapp Polymere) on a manual peptide synthesizer equipped with a Schmizo reactor. Before the elongation process, the resin was swelled in DMF for 2 to 3 hours and was washed with 240 mL of DMF (three times, 2 min/cycle). Following each coupling, the Fmoc groups were removed with 20% piperidine in 240 mL of DMF (three steps, 20 min each). In the case of Glu$^{17}$, Asn$^9$ and Gln$^4$, 2% HOBt was added to the deprotection solution. Following each deprotection, the resin was successively washed by 240 mL of DMF (4 times, 2 min/cycle), 240 mL of 2% HOBt in DMF (twice, 5 min/cycle), and 240 mL of DMF (twice, 2 min/cycle).

The amino acid couplings (1.5 to 2eq/amine) were performed in DMF (111 mL) at room temperature with DIC/HOBT (1.5 to 2eq each/amine) (see details below). The AA in positions 15-16 and 9-10 were incorporated as, respectively, Fmoc-Ile-Thr($\Psi^{Me,Me}$pro)-OH and Fmoc-Asn(Trt)-Ser($\Psi^{Me,Me}$pro)-OH. After 30 min, a fresh portion of DIC (1.5 to 2eq) was added to the reaction mixture. The coupling steps were monitored by the Kaiser test [1]. From Leu$^{18}$ to Ser$^1$, after 1 h coupling with DIC/HOBT (in equal amount), PyBOP reagent was added (see details below) and the pH was adjusted to 7 by dropwise addition of DIPEA. After 30 min, the resin was washed with 240 mL of DMF (5 times, 2 min/cycle) and an acetylation step was carried out from Leu$^{18}$ to Thr$^2$. The acetylation was performed at room temperature with acetic anhydride (1eq/amine) in the presence of pyridine (1 eq/amine) in 111 mL of DMF. After 20 min, the resin was washed with 240 mL of DMF (6 times, 2 min/cycle). After the incorporation of Tyr$^5$, the resin was extensively washed with 240 mL of DMF (8 times, 2 min/cycle) and 240 mL of CH$_2$Cl$_2$ (8 times, 2 min/cycle), before drying.

After the incorporation of Tyr$^5$, the assembly was pursued on a 0.15 mmol scale or a 4.65 mmol scale using the same protocole and afforded the peptide-resin 2 for, respectively, 4 and 5.

| | Amino acids (eq/amine, mmol) | DIC/HOBt: 1/1 (eq/amine, mmol) | Coupling reaction (min) | PyBOP (eq/ amine) |
|---|---|---|---|---|
| 20. | Fmoc-Lys(Fmoc)-OH (1.75, 2.1) | 1.75, 2.1 | 60 | 0.5 |
| 19. | Fmoc-Lys(Fmoc)-OH (2, 4.8) | 2, 4.8 | 105 | 1 |
| 18. | Fmoc-Leu-OH (2, 9.6) | 2, 9.6 | 60 | 1 |
| 17. | Fmoc-Glu(OtBu) (2, 9.6) | 2, 9.6 | 60 | 1 |
| 16-15. | Fmoc-Ile-Thr($\Psi^{Me-Me}$pro)-OH (1.5, 7.2) | 1.5, 7.2 | 60 | 0.5 |
| 14. | Fmoc-Gly-OH (2, 9.6) | 2, 9.6 | 60 | 1 |
| 13. | Fmoc-Ile-OH (2, 9.6) | 2, 9.6 | 60 | 1 |
| 12. | Fmoc-Phe-OH (2, 9.6) | 2, 9.6 | 60 | 1 |
| 11. | Fmoc-Lys(Boc)-OH (2 eq, 9.6 mmol) | 2, 9.6 | 60 | 1 |
| 10-9. | Fmoc-Asn(Trt)-Ser($\Psi^{Me-Me}$pro)-OH (1.5, 7.2) | 1.5, 7.2 | 60 | 0.5 |
| 8. | Fmoc-Ala-OH (2, 9.6) | 2, 9.6 | 60 | 1 |
| 7. | Fmoc-Lys(Boc)OH (2, 9.6) | 2, 9.6 | 60 | 1 |
| 6. | Fmoc-Ile-OH (2, 9.6) | 2, 9.6 | 60 | 1 |
| 5. | Fmoc-Tyr(tBu)OH (2, 9.6) | 2, 9.6 | 60 | 1 |
| 4. | Fmoc-Gln(Trt)-OH (2, 1.2 for 4) or (2, 37.2 for 5) | (2, 1.2) or (2, 37.2) | 60 | 1 |

[S(α-D-GalNAc(OAc)$_3$)-T(α-D-GalNAc(OAc)$_3$)-T(α-D-GalNAc(OAc)$_3$)-QYIKANSKFIGITEL]$_4$-K$_2$-K-β-Ala 4

The synthesis was performed from 2 (0.15 mmol) as previously described for 2. The coupling steps were performed with the following AA building blocks [5] and reagents.

| Amino acids (eq/amine, mmol) | DIC/HOBt: 1/1 (eq/amine, mmol) | Coupling reaction (min) | PyBOP (eq/amine) |
|---|---|---|---|
| 3. Fmoc-Thr(α-D-GalNAc(OAc)3)-OH (1.5, 0,9) | 1.5, 0.9 | 60 | 0.5 |
| 2. Fmoc-Thr(α-D-GalNAc(OAc)3)-OH (1.5, 0.9) | 1.5, 0.9 | 60 | 0.5 |
| 1. Fmoc-Ser(α-D-GalNAc(OAc)3)-OH (1.5, 0.9) | 1.5, 0.9 | 60 | 0.5 |

At the end of the synthesis, the glycopeptide-resin (0.15 mmol) was suspended in a TFA/TIS/H$_2$O(95/2.5/2.5 v/v/v) (10 mL/g of glycopeptide-resin) and stirred for 1 h at 20° C.=2° C. After filtration, the resin was washed twice with the same TFA mixture (2 mL/g of glycopeptide-resin per wash). The filtrates and the washes were gathered and stirred for additional 30 min at 20° C. ±2° C. After concentration (bath temperature ≤35° C.), the crude product was precipitated with DIPE (~35 mL/g of glycopeptide-resin). After filtration and washing with DIPE, the solid was dried (t°≤30° C.) and gave 750 mg of crude 4.

ESMS: 12409.589 ($C_{553}H_{855}N_{107}O_{213}$ calcd 12410,465)

[S(α-D-GalNAc(OBn)$_3$)-T(α-D-GalNAc(OBn)$_3$)-T(α-D-GalNAc(OBn)$_3$)-QYIKANSKFIGITEL]$_4$-K$_2$-K-β-Ala 5

The synthesis was performed from 2 (4.65 m/mol) as previously described for 2. The coupling steps were performed with the following AA building blocks (Ficher Chemicals AG) and reagents. At the end of the synthesis, 84.87 g of glycopeptide-resin were obtained.

| Amino acids (eq/amine, mmol) | DIC/HOBt: 1/1 (eq/amine, mmol) | Coupling reaction (min) | PyBOP (eq/amine) |
|---|---|---|---|
| 3. Fmoc-Thr(α-D-GalNAc(OBn)3)-OH (1.5, 27.9) | 1.5, 27.9 | 60 | 0.5 |
| 2. Fmoc-Thr(α-D-GalNAc(OBn)3)-OH (1.5, 27.9) | 1.5, 27.9 | 60 | 0.5 |
| 1. Fmoc-Ser(α-D-GalNAc(OBn)3)-OH (1.5, 27.9) | 1.5, 27.9 | 60 | 0.5 |

The glycopeptide-resin (20 g, 1.096 mmol) was treated as previously described for 4 and afforded 9.95 g of crude 5.

ESMS: 14141.433 ($C_{733}H_{999}N_{107}O_{177}$ calcd 14141,610)

Note: This protocol gave a comparable crude compound as that obtained according to protocol A, i.e. starting from Fmoc-β-Ala-p-benzyloxybenzyl alcohol resin (Wang resin) (see above).

[S(α-D-GalNAc(OH)$_3$)-T(α-D-GalNAc(OH)$_3$)-T(α-D-GalNAc(OH)$_3$)-QYIKANSKFIGITEL]$_4$-K$_2$-K-β-Ala or

MAG-Tn3  6

From 4

With Hydrazine [7]

100 mg (20 μmol) of 4 were dissolved in 3.2 mL of MeOH. 567 μL (11.3 mmol) of hydrazine monohydrate were added and the solution was stirred at room temperature. After 2 h30, the solution is cooled to 0° C. and 3.2 mL of acetone were added. After 1 h, the solution was concentrated and co-distilled five times with acetone. The crude glycopeptide was lyophilized to yield 117 mg. The product was purified by RP-HPLC using an Agilent 1200 pump system with a UV detector at 230 nm. The column was a Zorbax C18 (5μ, 300 Å, 9.4×250 mm) (Agilent) and the gradient was performed with water (0.1% TFA)/acetonitrile over 20 min, from 72/28 to 62/38. The purification gave 5.8 mg (net peptide content) of 6 in 96.4% purity. The overall yield is 2.7%.

With MeONa 24 mg (4.8 μmol) of 4 were dissolved in 3.2 mL of MeOH. The pH was adjusted to 14 (pH meter, moist pH paper ~10.5) with 1% MeONa in MeOH and the solution stirred at RT. The reaction was monitored by RP-HPLC. After 2 h, the reaction is neutralized with dry ice and evaporated to dryness. The crude peptide was dissolved in 1% aqueous TFA and lyophilized. The product was purified by RP-HPLC using an Agilent 1200 pump system with a UV detector at 230 nm. The column was a Kromasil C4 (5μ, 100 Å, 10×250 mm) (AIT) and the gradient was performed with 0.1% aqueous TFA (VWR)/acetonitrile (Carlo Erba) over 30 min, from 73/27 to 62/38. The purification gave 754 μg (net peptide content) of 6 in 91.4% purity. The overall yield is 1.4%.

From 5,

With H$_2$ 10 g (1.1 mmol) of 5 were dissolved in 800 mL of NMP/H$_2$O 87.5112.5. After addition of 4 g of 10% Pd/C type 39 (Johnson Matthey), the reaction was stirred at 37° C. and 5 bar for 170 h. Two additional amounts of catalyst were added portionwise after 72 h (2 g) and 120 h (2 g). At the end of the reaction, the catalyst was filtrated on celite and washed with NMP/H$_2$O 87.5112.5. The resulting filtrate was gathered with other filtrates issued from similar reaction (1.35 mmol in total). After dilution with H$_2$O (until NMP/H$_2$O 10/90), the filtrates were purified by RP-HPLC in two steps. The primary purification was carried out on a Vydac C18 column (300 Å, 10-15 μm, 50 mL/mn) with TFA/H$_2$O/CH$_3$CN 0.1/94.9/5.0 v/v/v (A) and with TFA/H$_2$O/CH$_3$CN 0.1/49.9/50.0 v/v/v (B). The gradient was 0% B over 15 min, 0-40% B over 5 min, 40-80% B over 60 min. The secondary purification was carried out on a Vydac C18 column (300 Å, 10-15 μm, 50 mL/mn) with AcOH/H$_2$O/CH$_3$CN 0.5194.5/5.0 v/v/v (A) and with AcOH/H$_2$O/CH$_3$CN 0.5/49.5/50.0 v/v/v (B). The gradient was 0% B over 15 min, 0-20% B over 5 min, 20-60% B over 60 min. After concentration by RP-HPLC on a Daisogel SP-300-10-ODS-AP column (20 mL/mn, isocratic TFA/H$_2$O/CH$_3$CN 0.1/49.9/50.0 v/v/v), the solution was evaporated on rotary evaporator and lyophilized to afford 225 mg (net peptide content) of 6 in 95.3% purity. The overall yield is 1.5%.

ESMS: 10897.387 ($C_{481}H_{783}N_{107}O_{177}$ calcd 10897,123)

Conclusion

The obtained results are summarized in the following table:

|  | Initial process I[1] | New process II | | | |
|---|---|---|---|---|---|
| Carbohydrate protective group (R) | None (H) | TBS | Ac | Bn | |
| Deprotection method | — | TFA | $NH_2$—$NH_2$ | TfOH | $H_2$ |
| Overall yield[2] (Purity)[3] | 1-10 mg scale 3% (94.5%) >10 mg scale <1% (<95%) | — | 2.7% (96.4%) | 1.6% (95.9%) | 1.5% (95.3%) |
| Comment Scale[4] | Impurities and reproducibility issues during scale-up => new synthesis route with carbohydrate protection | No expected compound (partial deprotection) Impurities++ | Scale ~5 mg | Compromise between complete deprotection and degradation. Scale ~5 mg | Scale 225 mg |

[1]ref 5 and 9, (Ref 11 of WO 9843677 Multiple antigen glycopeptide carbohydrate, vaccine comprising the same and use thereof)
[2]calculated on the net peptide content from the Fmoc-βAla-resin substitution (includes all the synthesis steps from 1).
[3]as determined by RP-HPLC: Column Zorbax 300SB C18 (3.5µ, 3 × 150 mm) (Agilent), 0.8 mL/min, A: acetonitrile + 0.1% TFA, B: water + 0.1% TFA, gradient 13% to 53% of A over 40 min, detection at 220 nm.
[4]Refers to the final product (net peptide content)

Compared to the initial synthesis using unprotected carbohydrate synthons (FIGS. 1 and 2), the new process (involving protected carbohydrates, II, FIGS. 1 and 2) allows to:

minimize the synthesis side-products
improve the process repeatability
scale-up the synthesis in a repeatable manner Among the tested protocols in the new process (Table, FIGS. 1 and 2), three emerge as the best strategies: Ac/Hydrazine, Bn/TfOH and Bn/$H_2$ (protecting group/deprotection method) (Table). They all led to the MAG-Tn3 with a purity ≥95%, in a repeatable manner.

The Bn/TfOH method afforded the MAG-Tn3 with an overall yield of 1.6%. This method relies on a compromise between complete deprotection and degradation. Alternatively, the Bn/$H_2$ method afforded the MAG-Tn3 with similar yield (1.5%) and, most importantly, the process has been validated on a 225 mg scale. Finally the Ac/hydrazine method gave the highest overall yield (2.7%, compared to 1.6% and 1.5%).

A MAG-Tn3 based on another peptide (PV=KLFAVWKITYKDT) (SEQ ID No 4) has also been prepared according to the method of invention (Ac/Hydrazine, Bn/TfOH).)

Example 2: Influence of the Resin Substitution Ratio and of the Nature of the Stationary Phase used for the Purification of MAG-Tn3

MAG-Tn3 was prepared according to protocol B from a polystyrene resin functionalized with Fmoc-β-Ala (sold under the trade name Fmoc-β-Ala-TentaGel R Trt), with two different substitution ratios: 0.13 or 0.1 mmol/g (namely the number of Fmoc-β-Ala grafted groups relative to the weight of the non grafted resin).

The purification of the crude MAG-Tn3 was then performed by RP-HPLC on three distinct stationary phases (reversed phases) based on a silica gel grafted by octadecyl groups, namely Vydac®, Jupiter® and Daisogel®. The primary purification was carried out with TFA/$H_2O$/$CH_3CN$ 0.1194.9/5.0 v/v/v (A) and with TFA/$H_2O$/$CH_3CN$ 0.1/49.9/50.0 v/v/v (B). The gradient was 0% B over 15 min, 0-40% B over 5 min, 40-80% B over 60 min. The secondary purification was carried out with AcOH/$H_2O$/$CH_3CN$ 0.5/94.5/5.0 v/v/v (A) and with AcOH/$H_2O$/$CH_3CN$ 0.5/49.5/50.0 v/v/v (B). The gradient was 0% B over 15 min, 0-20% B over 5 min, 20-60% B over 60 min.

The results are reported in the following table.

| MAG-Tn3 batch | Resin substitution (mmol/g) | Purification stationary phase | Quantity (g)[a] | Purity (%)[b] | Overall yield (%)[c] |
|---|---|---|---|---|---|
| 1 | 0.13 | Vydac® | 0.275 | 95.3 | 2-4 |
| 2 | 0.13 | Jupiter® | 3.63 | 96.6 | 6 |
| 3 | 0.1 | Daisogel® | 4.65 | 99.2 | 11 |
| 4 | 0.1 | Daisogel® | 4.72 | 99.0 | 11 |

[a]Powder weight
[b]Analysis by RP-HPLC: Zorbax 300SB C18 (3.5µ, 3 × 150 mm, Agilent), A: acetonitrile + 0.1% TFA, B: $H_2O$ + 0.1% TFA, 15-53% A (40 min).
[c]The yield includes all the synthetic steps from Fmoc-β-Ala-resin and was calculated on the net peptide content of the final product.
Vydac® C18, 300 Å, 10-15 µm (Grace), ref 218MSB1015 or 218TPB1015 or 238TPB1015
Jupiter® C18, 300 Å, 10 µm (Phenomenex), ref 04G-4055
Daisogel® C18, 300 Å, 10 µm (Daiso), ref SP-300-10-ODS-RPS These results demonstrate that both the yields of the process of preparation of the conjugates according to the invention, and the purity of the obtained conjugates can be highly improved by reducing the substitution ratio of the resin and/or by using an appropriate stationary phase.

REFERENCES

1. Kaiser, E., R. L. Colescott, C. D. Bossinger, and P. I. Cook, Anal Biochem (1970). 34: 595-8.
2. Maemura, M., A. Ohgaki, Y. Nakahara, H. Hojo, and Y. Nakahara, Bioscience Biotechnology and Biochemistry (2005). 69: 1575-1583.
3. Tam, J. P., W. F. Heath, and R. B. Merrifield, J Am Chem Soc (1986). 108: 5242-5251.
4. Tanaka, E., Y. Nakahara, Y. Kuroda, Y. Takano, N. Kojima, H. Hojo, and Y. Nakahara, Bioscience Biotechnology and Biochemistry (2006). 70: 2515-2522.
5. Bay, S., R. Lo-Man, E. Osinaga, H. Nakada, C. Leclerc, and D. Cantacuzène, J. Peptide Res. (1997). 49: 620-625;

6.: Fmoc solid phase peptide synthesis, A practical approach, Edited by W. C. Chan and P. D. White, Oxford University Press.

7. Sander, J. and H. Waldmann, Chem Eur J (2000). 6: 1564-1577.

8. Lo-Man, R., S. Vichier-Guerre, S. Bay, E. Dériaud, D. Cantacuzène, and C. Leclerc, J. Immunol. (2001). 166: 2849-2854.

9. La-Man, R., S. Vichier-Guerre, R. Perraut, E. Dériaud, V. Huteau, L. BenMohamed, O. M. Diop, P. O. Livingston, S. Bay, and C. Leclerc, Cancer Res (2004). 64: 4987-4994

10. Babino, A., D. Tello, A. Rojas, S. Bay, E. Osinaga, and P. M. Alzari, FEBS Lett. (2003). 536: 106-110.

11. WO9843677—Multiple antigen glycopeptide carbohydrate, vaccine comprising the same and use thereof

The invention claimed is:

1. A method for preparing a carbohydrate T cell epitope conjugate of formula (I):

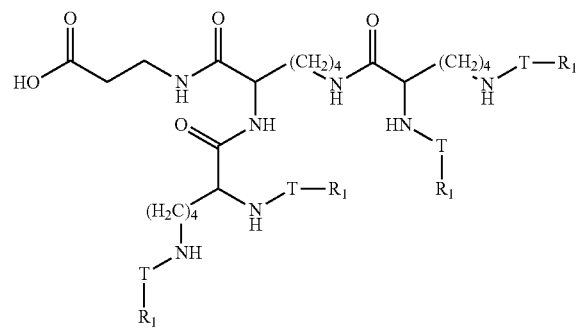
(I)

wherein

T is a peptide QYIKANSKFIGITEL (SEQ ID NO: 1); and $R_1$ is:

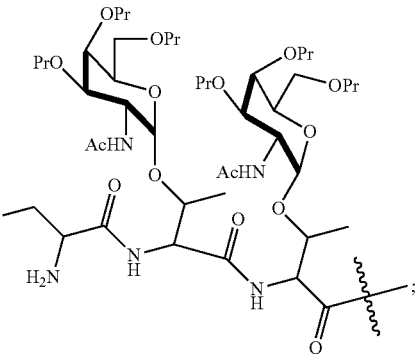

and the Pr groups are selected from benzyl and acetyl.

2. The method of claim 1, wherein the Pr protecting groups are benzyl.

3. The method of claim 2, wherein the benzyl groups are removed in the presence of TfOH or $H_2$.

4. The method of claim 1, wherein the Pr protecting groups are acetyl.

5. The method of claim 4, wherein the acetyl groups are removed in the presence of hydrazine or MeONa.

6. A method for preparing a carbohydrate T cell epitope conjugate immobilized on a solid support, Z, via a β-Ala-residue, said T cell epitope conjugate having formula (III):

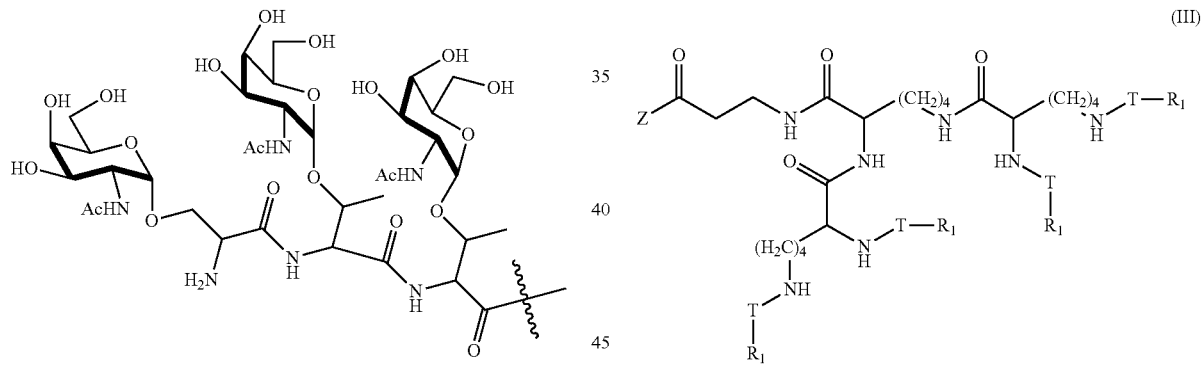
(III)

wherein

T is a peptide QYIKANSKFIGITEL (SEQ ID NO: 1);

$R_1$ is:

said method comprising the step of removing the Pr protecting groups from a compound of formula (II)

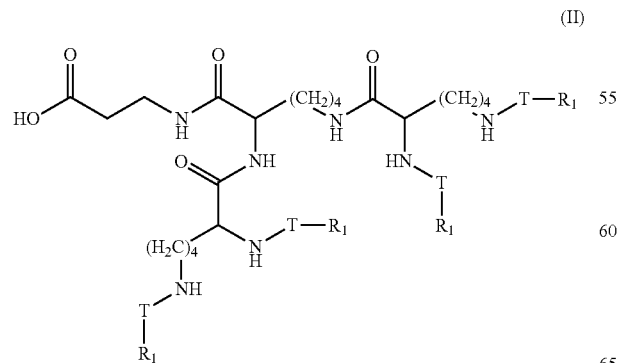
(II)

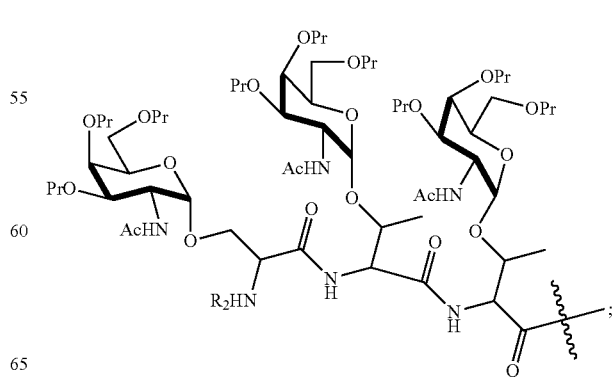

and

Pr are protecting groups, said protecting groups selected from benzyl and acetyl;

$R_2$ is Fmoc or H;

said method comprising the step of coupling compounds of formula (IV):

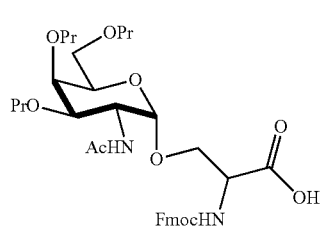
(IV)

to a compound immobilized on a solid support via a β-Ala-residue, said compound immobilized on a solid support, Z, having formula (V):

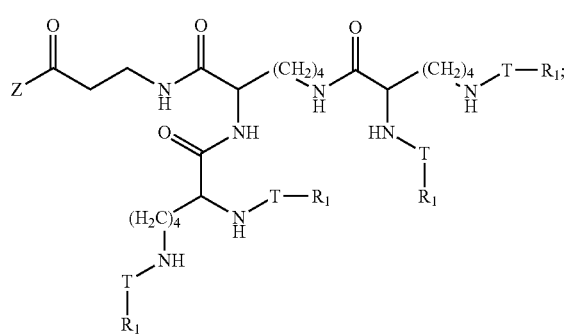
(V)

wherein

T is a peptide QYIKANSKFIGITEL (SEQ ID NO: 1) and $R_1$ is

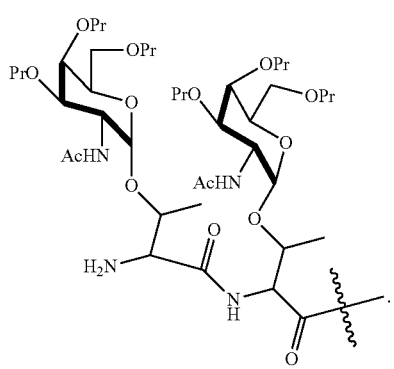

7. The method of claim 6, wherein the Pr protecting groups are benzyl.

8. The method of claim 6, wherein the Pr protecting groups are acetyl.

9. The method of claim 7, wherein $R_2$ is Fmoc.

10. The method of claim 7, wherein $R_2$ is H.

11. The method of claim 8, wherein $R_2$ is Fmoc.

12. The method of claim 8, wherein $R_2$ is H.

13. The method of claim 6, wherein $R_2$ is H.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 2

Phe Asn Asn Phe Thr Val Ser Phe Trp Leu Arg Val Pro Lys Val Ser
1               5                   10                  15

Ala Ser His Leu Glu
            20

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 3

Gly Gln Ile Gly Asn Asp Pro Asn Arg Asp Ile Leu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 4

Lys Leu Phe Ala Val Trp Lys Ile Thr Tyr Lys Asp Thr
1               5                   10
```